(12) United States Patent
Lurie

(10) Patent No.: US 6,796,053 B2
(45) Date of Patent: Sep. 28, 2004

(54) PORTABLE FORCED AIR APPAREL AND EQUIPMENT DRYING, DEODORIZING AND SCENTING SYSTEM

(76) Inventor: Glenn Lurie, 4 Kentsdale Dr., Pennington, NJ (US) 08534

( * ) Notice: Subject to any disclaimer, the term of this patent is extended or adjusted under 35 U.S.C. 154(b) by 0 days.

(21) Appl. No.: 10/662,462

(22) Filed: Sep. 16, 2003

(65) Prior Publication Data

US 2004/0068888 A1 Apr. 15, 2004

Related U.S. Application Data

(60) Provisional application No. 60/417,242, filed on Oct. 9, 2002.

(51) Int. Cl.[7] .................................................. F26B 25/00
(52) U.S. Cl. ........................... 34/104; 34/90; 34/239
(58) Field of Search ....................... 34/90, 103, 104, 34/106, 114, 115, 124, 209, 210, 215, 218, 239, 487, 492

(56) References Cited

U.S. PATENT DOCUMENTS

| | | | | |
|---|---|---|---|---|
| 3,793,744 A | * | 2/1974 | Saita ........................... 34/104 |
| 4,967,060 A | * | 10/1990 | Lomeli ......................... 392/384 |
| 5,222,308 A | * | 6/1993 | Barker et al. .................. 34/104 |
| 5,289,642 A | * | 3/1994 | Sloan ........................... 34/104 |

* cited by examiner

Primary Examiner—Jiping Lu
(74) Attorney, Agent, or Firm—Sperry, Zoda & Kane

(57) ABSTRACT

A portable apparatus for drying articles which includes a blower with a main conduit. A distributing manifold is adapted to receive drying air from the main conduit. This distributing manifold defines a plurality of manifold outlets therein. Each manifold outlet includes a similarly configured manifold attachment device. A plurality of drying fixtures are included each having a unique configuration for drying a particular article, such as articles of clothing. Each drying fixture includes a connecting section for receiving air and a hanging section for receiving air from the connecting section. The hanging section defines a plurality of holes for allowing drying air to exit therefrom. Each drying fixture includes a fixture attachment device detachably securable to any one of the manifold attachment devices thereby providing variability in the location and configuration for use of this apparatus. Each drying fixture includes a valve.

28 Claims, 10 Drawing Sheets

PORTABLE FORCED AIR APPAREL AND EQUIPMENT DRYING, DEODORIZING AND SCENTING SYSTEM

This application claims filing priority based upon U.S. provisional patent application No. 60/417,242, filed Oct. 9, 2002 on a Portable Forced Air Apparel And Equipment Drying, Deodorizing And Scenting System, filed by applicant, Glenn Lurie, currently pending.

BACKGROUND OF THE INVENTION

1. Field of the Invention

The present invention deals with the field of devices for generally drying of articles which are normally hung such as on a drying rack or line after excessive use or after washing thereof. The present device provides a unique air flow configuration including a blower connected through a plurality of conduits which can provide various capabilities. As such, the present invention provides a uniquely improved configuration for a drying rack which includes the possibility for scenting thereof, deodorizing thereof and wherein the drying rack includes a plurality of holes in uniquely defined zones for dispensing air therefrom to enhance drying of articles such as clothing or the like hung in these hanging conduit sections. Furthermore the present invention provides a means for varying the configuration of the drying fixtures in an almost infinite number of ways since each drying fixture is itself separately attachable with respect to each manifold attachment device positioned at each manifold outlet of the air distributing manifold defined here within.

2. Description of the Prior Art

Various devices have been patented for the purpose of causing air flow to facilitate drying of articles in various manners which are positioned upon various implements to enhance drying thereof such as shown in U.S. Pat. No. 4,136,464 patented Jan. 30, 1979 to A. Hay on a "Boot Drying Apparatus"; and U.S. Pat. No. 4,697,724 patented Oct. 6, 1987 to B. Pitcher on a "Resilient Glove Tree"; and U.S. Pat. No. 5,058,289 patented Oct. 22, 1991 to A. Guindon on a "Garment Drying Apparatus"; and U.S. Pat. No. 5,117,565 patented Jun. 2, 1992 to T. H. Willenbacher on a "Glove Drying Apparatus"; and U.S. Pat. No. 5,125,169 patented Jun. 30, 1992 to M. F. Bader and assigned to Protonaut, Inc. on a "Glove Drying Apparatus And Method"; and U.S. Pat. No. 5,199,188 patented Apr. 6, 1993 to D. Franz on a "Method And Apparatus For Drying Footwear And Handwear"; and U.S. Pat. No. 5,249,369 patented Oct. 5, 1993 to M. Mallet on a "Method And Apparatus For Drying The Interior Surfaces of Hollow Articles Such As Air Rebreathing Or Resuscitator Bags"; and U.S. Pat. No. 5,287,636 patented Feb. 22, 1994 to A. Lafleur et al and assigned to Colette Laferriere and Lise Laferriere on a "Tubular Drying Apparatus For Footwear Or Handwear"; and U.S. Pat. No. 5,379,525 patented Jan. 10, 1995 to G. T. Taynor on a "Drying Stand For Ski Boots, Gloves And The Like"; and U.S. Pat. No. 5,394,619 patented Mar. 7, 1995 to B. E. Kaplan on a "Portable Clothes Dryer And Room Humidifier"; and U.S. Pat. No. 5,406,717 patented Apr. 18, 1995 to C. M. Dofka on a "Drying Rack For Utility Gloves"; and U.S. Pat. No. 5,412,928 patented May 9, 1995 to F. Reithel on a "Dehydration Device"; and U.S. Pat. No. 5,592,750 patented Jan. 14, 1997 to G. Eichten on a "Portable Clothing And Equipment Drier"; and U.S. Pat. No. 5,604,993 patented Feb. 25, 1997 to I. G. Auckerman on "Glove Drying Devices And Methods"; and U.S. Pat. No. 5,862,606 patented Jan. 26, 1999 to H. Jannach on a "Device For Drying, Washing And/Or Disinfecting Protective Suits"; and U.S. Pat. No. 5,862,924 patented Jan. 26, 1999 to G. Dumont on a "Rack For Sports Equipment"; and U.S. Design Pat. No. Des.355,288 patented Feb. 7, 1995 to F. Mallen and assigned to Dalenger Inc. on a "Rack For Hanging/Drying Sports Equipment"; and U.S. Design Pat. No. Des.394,926 patented Jun. 2, 1998 to S. Lindsay on a "Hockey Equipment Dryer"; and U.S. Pat. No. 5,953,830 patented Sep. 21, 1999 to H, Jannach and assigned to Helmut Jannach on an "Apparatus For Drying Clothing, Jackets Or The Like"; and U.S. Pat. No. 6,005,227 patented Dec. 21, 1999 to S. Pappas on a "Towel Warmer Console Cabinet"; and U.S. Pat. No. 6,216,887 patented Apr. 17, 2001 to M. Soo on a "Detachable Hanger For Sport Pads"; and U.S. Pat. No. 6,327,792 patented Dec. 11, 2001 to D. L. Hebert on a "Portable And Collapsible Sports Dryer".

SUMMARY OF THE INVENTION

In the improved portable apparatus for drying articles of the present invention a blower is preferably included which can optionally include a heating means therewithin to facilitate supplying of air which may be heated for drying of the articles. The blower is attached directly with respect to a main conduit. This main conduit defines a main duct extending therewithin which is capable of carrying air flow. The main conduit also defines a main conduit inlet to which the blower is attached for supplying of air thereto. The main conduit inlet is in fluid flow communication with respect to the main duct to facilitate air flowing into the main duct through the main duct inlet. Furthermore a main duct outlet is defined within the main duct which is also in fluid flow communication with the main duct to allow air supplied into the main conduit to exit therefrom. The main conduit can further define a scenting chamber therewithin for selectively holding of a scenting material for applying an aroma to the drying air as it passes through the main duct if desired.

A distributing manifold is also included which may define a manifold duct extending throughout the interior thereof. This distributing manifold preferably defines a manifold inlet in fluid flow communication with respect to the manifold duct for facilitating air flow therebetween. The manifold inlet is preferably operatively attached with respect to the main conduit outlet to receive air exiting therefrom. The distributing manifold will define a plurality of manifold outlets at one or more locations therein. A plurality of manifold attachment devices will be included with one mounted within each of the manifold outlets to facilitate detachable securement thereto of one of the drying fixtures.

The present invention further defines a plurality of drying fixtures with each being detachably secured with respect to any single manifold outlet for receiving air flow therefrom. Each of these drying fixtures provide a contour for holding of drying articles of various specific pre-defined shapes.

There are many common aspects among the drying fixtures such as the inclusion of a connecting conduit section. Each drying section will include such a connecting conduit section which will define a connecting section duct extending therethrough for carrying air. The connecting conduit section will not define any apertures therein since it is designed to support the drying fixture and connect it to the distributing manifold while conveying air through the connecting section duct to the portion of the drying fixture which does include holes for drying. The connecting conduit section further defines a drying fixture opening therewithin in fluid flow communication with respect to the connecting section duct.

A fixture attachment device is mounted on each of the connecting conduit sections adjacent to the drying fixture opening such that it is selectively securable with respect to any one of the manifold attachment devices to detachably mount one of the drying fixtures with respect to the distributing manifold at one of a variety of choosable locations in order to allow fluid flow communication between the distributing manifold outlet and the drying fixture opening to facilitate air flow into the connecting section duct of the drying fixture for facilitating drying therewith.

A hanging conduit section will be included within each drying fixture which defines a hanging section duct extending therewithin. The hanging section duct is positioned in fluid flow communication with respect to the connecting section duct in order to receive air flow therefrom. The hanging conduit section itself will define a plurality of drying holes therewithin which are in fluid flow communication with respect to the hanging section duct for the dispensing of air outwardly therefrom for drying of an article positioned thereadjacent. The hanging conduit section is adapted to receive an article detachably held thereadjacent in order to facilitate drying thereof as air flow outwardly therefrom through the drying holes. The hanging conduit section of each of the drying fixtures is preferably of an adjustable size. This adjustable size is caused by the inclusion of a first hanging member and a second hanging member which are movably mounted with respect to one another.

The first hanging member preferably will define a portion of the hanging section duct therewithin and will define a plurality of drying holes therewithin. The second hanging member will define preferably the remaining portion of the hanging section duct therewithin and will also define a plurality of drying holes. The second hanging member is preferably positioned in telescoping engagement with respect to the first hanging member such as to be movable in telescopic manner with respect thereto to vary the overall dimensions of the hanging conduit section of the drying fixture and in this manner greatly facilitate usage thereof by allowing articles of various sizes to be dried thereupon.

A fixture valve is preferably positioned within the connecting conduit section of each of the drying fixtures and extends thereacross to control the air flow through the connecting section duct. Each of these fixture valves is preferably movable to a completely opened position to allow full air flow through the connecting conduit section of the drying fixture and to a completely closed position to prevent air flow through the connecting conduit section of the drying fixture. Preferably the fixture valve can also be movable to any intermediate position therebetween to in some manner restrict the air flow through the connecting conduit section of the drying fixture.

In the preferred configuration of the present invention the main conduit will define an access opening therein which provides access to the scenting chamber to facilitate maintenance such as the replacement of the scenting means located therein after it has been significantly depleted. An access door may be also included movable between a closed position extending across the access opening for sealing thereof and an opened position for providing access through the access opening into the scenting chamber for further facilitating maintenance.

As described above the present invention is particularly usable with articles, particularly articles of clothing having various sizes. The size of various pieces of athletic equipment or other clothing or protective gear that need to be dried can vary significantly in size and in some cases shape. To accommodate this variation in shape as described above the hanging conduit section can be formed of two or more telescopically engaging hanging members. Once the relative position of these parts is chosen for the specific article being dried, it is preferable that the adjustable positioning between these parts be restricted or further prevented. This can be achieved by the inclusion of one or more set screws engageable with respect to the first hanging member and the second hanging member for the purpose of selectively preventing relative movement therebetween.

In a further preferred embodiment of the present invention a deodorizing device may be attachable with respect to the drying fixture at various locations thereupon to facilitate deodorizing of articles while they are being dried thereupon.

In one chosen configuration of the present design the distributing manifold will include a first manifold member secured with respect to the main conduit such as to have a fixed configuration and be immovable. This fixed manifold member will define the manifold inlet. This manifold inlet will be positioned by the first manifold member in fluid flow communication with respect to the main conduit outlet in order to facilitate air flow therebetween. The fixed manifold member will define a first manifold outlet and a second manifold outlet therein. The fixed manifold member will also define a left fixed manifold exit aperture and a right fixed manifold exit aperture.

The distributing manifold preferably will also include two adjustable manifold sections secured thereto. In particular a left adjustable manifold member will preferably be detachably secured with respect to the left fixed manifold exit aperture for receiving air flow therefrom. This left adjustable manifold member will be of an adjustable configuration to vary the positions of the fixtures when attached with respect thereto.

In a similar manner a right adjustable manifold member will be detachably secured with respect to the right fixed manifold exit aperture for receiving air flow therefrom. This right adjustable manifold member will have an adjustable configuration as desired. The specific configuration of the left adjustable manifold member and the right adjustable manifold member can be similar. However, normally they will define between two and ten manifold attachment devices to which any one of the one through ten or even greater number of drying fixtures may be attached. By the capability of variable positioning of the drying fixtures relative to the left and right adjustable manifold members, the present invention will provide a uniquely reconfigurable design completely different from anything available or known in the prior art. Furthermore in the preferred configuration a first left valve means will be positioned within the first left adjustable conduit to control air flow therethrough and similarly a second left valve will be positioned within the second left adjustable conduit section to control air flow therethrough. In this manner individual sections of the apparatus can be closed completely or have restricted flow thereto in order to vary the overall drying capabilities of the design of the present invention.

The drying fixtures of the present invention can have various configurations. In particular a glove fixture can be included wherein the hanging conduit section thereof includes a hand loop section generally shaped in a circular manner as well as a thumb section which is shaped in a generally longitudinally extending manner. The hand loop section and thumb section are preferably positioned adjacent to one another to facilitate placement of a glove thereon for enhancing drying.

Another configuration for the fixture can comprise a helmet or headgear fixture wherein the hanging conduit section thereof includes a rounded head section and wherein the connecting conduit section includes a chin support section which is defined in a plane immediately adjacent to the rounded head section for facilitating placement of head gear thereupon and enhancing drying thereof.

Another alternative configuration for the drying fixture is as a footwear fixture wherein the hanging conduit section thereof includes a plurality of L-shaped loop sections to facilitate placement of footwear thereupon for enhanced drying.

A long pants fixture may also be included wherein the hanging conduit section includes a first pants section and a second pants section positioned spatially apart and extending generally parallel with respect to one another. The first and second pants section preferably will each be of a tapered cylindrical shape to facilitate placement of long pants thereon for enhanced drying.

A protective cup shorts fixture may also be included wherein the hanging conduit section includes a first short pants section and second short pants section as well as a crotch cup drying zone for use with shorts designed to hold a cup or other protective gear therewithin.

An upper body fixture may also be included wherein the hanging conduit section thereof includes a rounded chest section and a first arm section extending outwardly and downwardly therefrom. Also a second arm section can extend outwardly and downwardly therefrom to enhance drying of any upper body fixture such as a jersey shirt or jacket.

A leg protector fixture may also be included which includes a first longitudinal section and a second longitudinal section each shaped generally longitudinally cylindrical and oriented generally parallel with respect to one another to facilitate placement of leg protecting members thereupon. This device is particularly usable with leg protecting fixtures such as shin guards or goalie leg pads.

An elbow pad fixture may also be included in the apparatus of the present invention wherein the hanging conduit section defines a first upper arm section and a first lower arm section extending longitudinally and oriented at an obtuse angle with respect to one another. The hanging conduit section further includes a second upper arm section and a second lower arm section extending longitudinally and oriented in an obtuse angle with respect to one another to facilitate drying of various configurations of elbow pads.

A chest protection fixture can be included wherein the hanging conduit section thereof includes a rectangular chest section and a left arm section extending outwardly and downwardly and a right arm section extending similarly. Such a chest protection fixture is usable for drying of shoulder pads or other chest or upper body protection apparatus.

It is an object of the present invention to provide a portable apparatus for drying articles which is infinitely configurable.

It is an object of the present invention to provide a portable apparatus for drying articles which includes a plurality of manifold attachment means each of which can be connected to any one of a plurality of drying fixtures to facilitate variation in the configuration thereof.

It is an object of the present invention to provide a portable apparatus for drying articles which can include a means for deodorizing while drying.

It is an object of the present invention to provide a portable apparatus for drying articles which can include a means for scenting while drying.

It is an object of the present invention to provide a portable apparatus for drying articles which includes adjustable sections for providing variation and adjustability in the relative positioning of a plurality of drying fixtures with respect to one another.

It is an object of the present invention to provide a portable apparatus for drying articles which provides a plurality of drying fixtures each having a unique configuration adaptable for drying of a particular article of clothing.

It is an object of the present invention to provide a portable apparatus for drying articles which provides a hanging conduit section for hanging of articles for drying within a specific drying fixture wherein the length and/or size of the hanging conduit is variable by defining it with two or more telescopically engageable sections.

It is an object of the present invention to provide a portable apparatus for drying articles which can include capping means for limiting air flow in selected areas within the apparatus.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
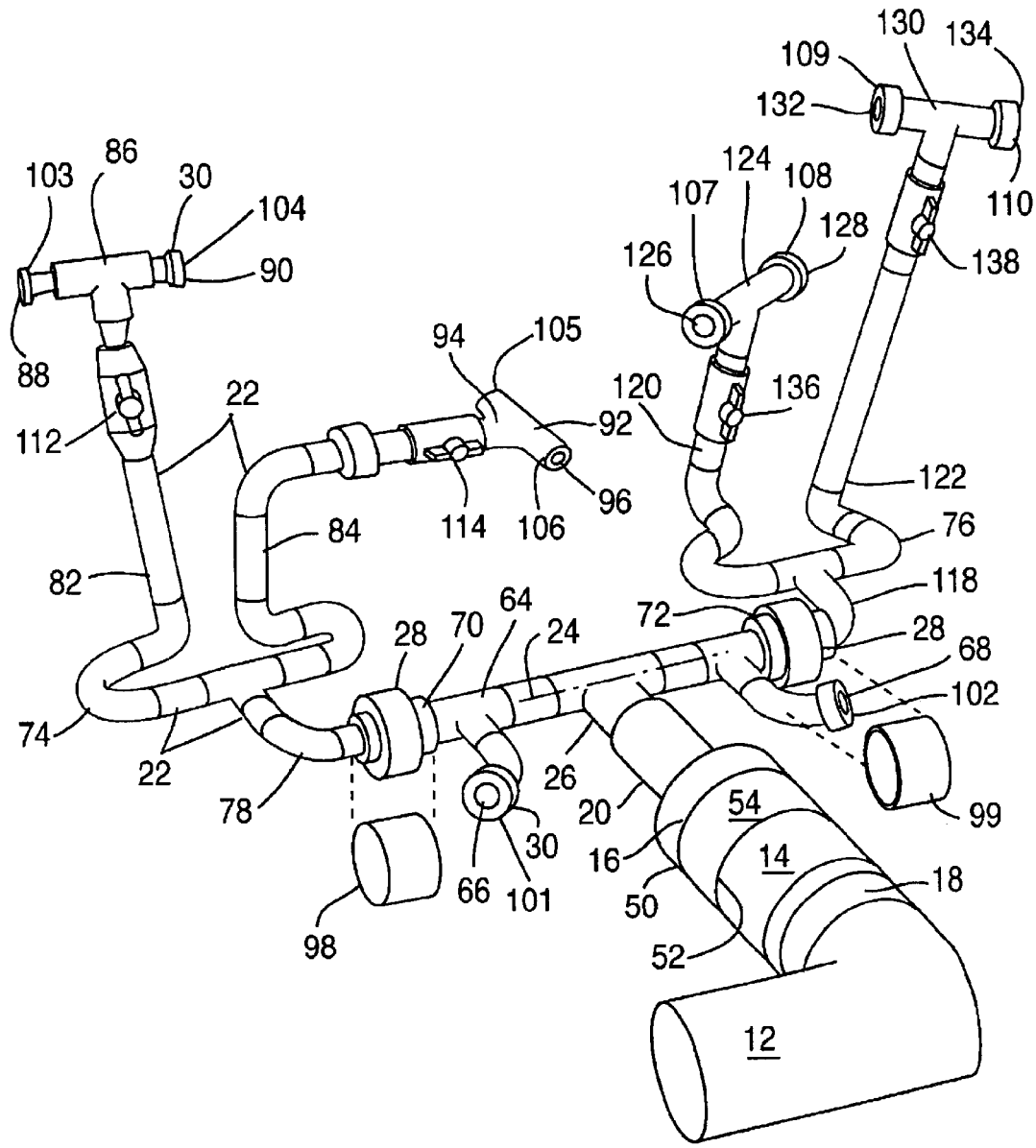
FIG. 1 is a perspective illustration of an embodiment of the blower, main conduit and distributing manifold of the present invention.

The present invention as depicted in the embodiment shown in FIG. 1 shows a portable apparatus for drying of articles 10. The articles to be dried can be any type of article but preferably would be clothing and in the currently perceived most common use for this apparatus, the articles will be sporting equipment. Such sporting equipment should be washed in between sporting events and often times these events are in locations where a conventional washer and dryer is not available. Other times the washing of such garments is not possible and therefore it is necessary to dry them to remove perspiration therefrom in between uses within very short time periods. As such, the portable apparatus of the present invention is particularly usable for drying of articles of clothing for sporting activities such as ice or in-line hockey, soccer, basketball, football, lacrosse, baseball or other outdoor activities such as hunting, fishing or skiing.

It is also important that the apparatus of the present invention be lightweight and portable. The apparatus as disclosed in the present invention can be hung from any type of door and preferably would be hung over the uppermost edge of such door. Alternatively, the present invention can be mounted upon a door or wall or any other vertically extending surface. In a third embodiment an integrated mounting board can be utilized as a table and include downwardly extending legs for separate independent positioning as desired. With all of these uses the present invention still will maintain the basic configuration of the embodiment as shown in FIG. 1.

FIG. 1 shows that the apparatus of the present invention includes a blower 12 which can include a heating element therewithin optionally. Blower 12 is designed to provide air for drying to a main conduit 14. Main conduit 14 preferably defines a main duct 16 extending along the centerline 16. Main conduit 14 preferably defines a main conduit inlet 18 and a main conduit outlet 20 both in fluid flow communication with respect to the main duct 16. Main duct inlet 18 is adapted to receive air from the blower 12 for distribution of heated air.

A distributing manifold 22 is preferably included and is operatively connected with respect to the main conduit 14 to receive air therefrom. The distributing manifold 22 preferably defines a manifold duct 24 therewithin which is in fluid flow communication with a manifold inlet 26 and a manifold outlet 28 both also defined in the manifold 22. The manifold inlet 26 is fixedly secured with respect to the main conduit outlet 20 in such a manner as to receive air flow therefrom for drying.

The distributing manifold 22 will preferably define a plurality of manifold attachment devices 30. One of such manifold attachment devices 30 will be secured with respect to each manifold outlet 28 defined in the distributing manifold 22. Distributing manifold 22 can include as few as two such manifold outlets 28 or as many as ten or more such outlets. Each of these outlets however should include a manifold attachment device 30 positioned thereadjacent to facilitate securement of a drying fixture 32 thereto selectively.

The drying fixture 32 is detachably securable to the manifold attachment means 30 adjacent a manifold outlet 28 to receive air therefrom for drying. Drying fixture 32 can be formed of many different shapes, sizes or constructions to facilitate the drying of articles of different shape, size and configuration. It is an important aspect of the present invention that each drying fixture 32 can be secured with respect to the distributing manifold 22 by being secured to any one of the individual manifold outlets 28. In this manner a single particular chosen drying fixture 32 can be positioned in various orientations depending on the extent of drying required and other parameters.

Each drying fixture 32 will comprise basically two sections. Initially drying fixture 32 will include a connecting conduit section 34 and a hanging conduit section 42. The connecting conduit section 34 defines extending there throughout a connecting section duct 36. Also connecting conduit section 34 includes a drying fixture opening 38. The drying fixture opening 38 includes a fixture attachment means 40 mounted thereadjacent. Fixture attachment means 40 of each drying fixture 32 is attachable with respect to one of the manifold attachment devices 30 positioned at the manifold outlets 28 of distributing manifold 22. As such, since the fixture attachment device 40 is attachable with respect to any one of the manifold attachment devices 30, then the drying fixture 32 can be secured with respect to the distributing manifold 22 at any of the as many as ten or more manifold attachment means. This universal versatility allows the individual drying fixtures 32 to be positioned at many different locations. Also the present invention does provide a plurality of different configuration for the drying fixtures 32 and, as such, these are attachable in many different types of arrangements depending on the type of articles being washed, the type of articles to be dried and the environment in which they are being dried.

The drying fixture 32 also includes a hanging section 42. Hanging section 42 defines a plurality of drying holes 46 thereadjacent. Hanging section 42 is adapted to receive the article 10 to be dried positioned hanging thereover. Hanging section 42 is connected to the distributing manifold 22 by the connecting conduit section 34 of the drying fixture. Thus the drying fixture includes the non-perforated connecting conduit section 34 with the fixture attachment means 40 mounted therein and it also includes the hanging section 42 upon which the drying actually occurs. Hanging section 42 preferably includes a hanging section duct 44 extending therethrough for communicating air for drying to the drying holes 46 positioned thereover. The hanging section 42 is adapted to dispense the drying air outwardly in many different directions subject to the positioning of the drying holes 46. In this manner the hanging conduit section 42 will achieve drying of an article 10 positioned thereover. The purpose of the connecting section 34 is to space the hanging conduit section 42 outwardly from the distributing manifold 22 to allow an article 10 to be positioned spatially distant therefrom and hang downwardly from the hanging section 42. In the preferred embodiment the connecting section 34 will preferably include a fixture valve 48 positioned thereon. This fixture valve 48 is adapted to open to allow full air flow for drying to the associated fixture or to close and prevent air flow to a drying fixture in a situation where the particular drying fixture 32 is not being utilized or where the article 10 positioned hanging over the hanging section 42 thereof has already been dried.

The present invention may also include a scenting chamber 50 which preferably is defined within the main conduit 14. Scenting chamber 50 includes an access door 54 extending thereover and an access opening 52 immediately thereadjacent. Access door 54 is adapted to be movable between a closed position extending across the access opening 52 and limiting access into the scenting chamber 50 and an opened position wherein the access door 54 allows full access to the access opening 52 into the scenting chamber 50 for replacement of the scenting material located therewithin as needed.

One of the important improvements of the present invention is in the configuration of the hanging conduit section 42 of each drying fixture 32 to preferably include a telescoping interconnection 57 positioned between a first hanging member 56 and a second hanging member 58. First hanging member 56 is connected to the connecting section 34 as to be firmly secured with respect thereto. The second hanging member 58 is telescopically engageable and movable with respect to the first hanging member 56 through the telescoping interconnection 57 therebetween. In this manner movement of the second hanging member 58 away from the first hanging member 56 will expand the overall size of the hanging conduit section 42. This will be necessary when used with articles 10 to be dried which are of a larger size but similar configuration. On the other hand for articles 10 which are somewhat smaller the second hanging member 58 can be moved toward the first hanging member 56 through the telescoping interconnection 57 therebetween thereby decreasing the overall size of the hanging conduit section 42 and facilitating drying of smaller items as well as allowing further compacting of the apparatus of the present invention for enhancing portability thereof. A set screw 60 may be engageable with respect to the first hanging member 56 and the second hanging member 58 to lock it in position and prevent further movability of the telescoping interconnection 57 when the set screw 60 is in the locked position. Set screw 60 is movable to the unlocked or disengaged position to allow relative telescoping movement of the second hanging member 58 with respect to the first hanging member 56.

Figure 7:
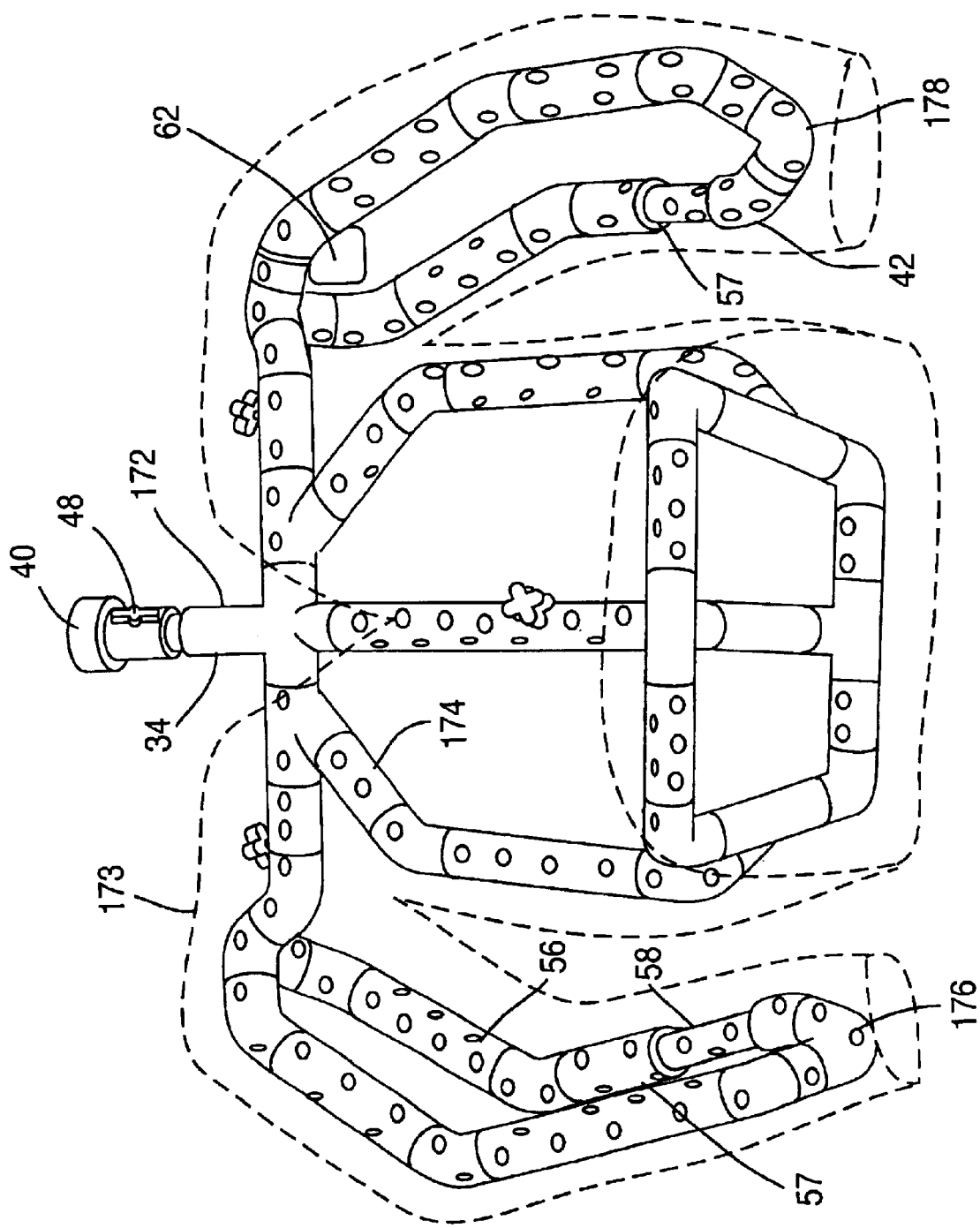
FIG. 7 is a perspective illustration of an upper body drying fixture.
Figure 9:
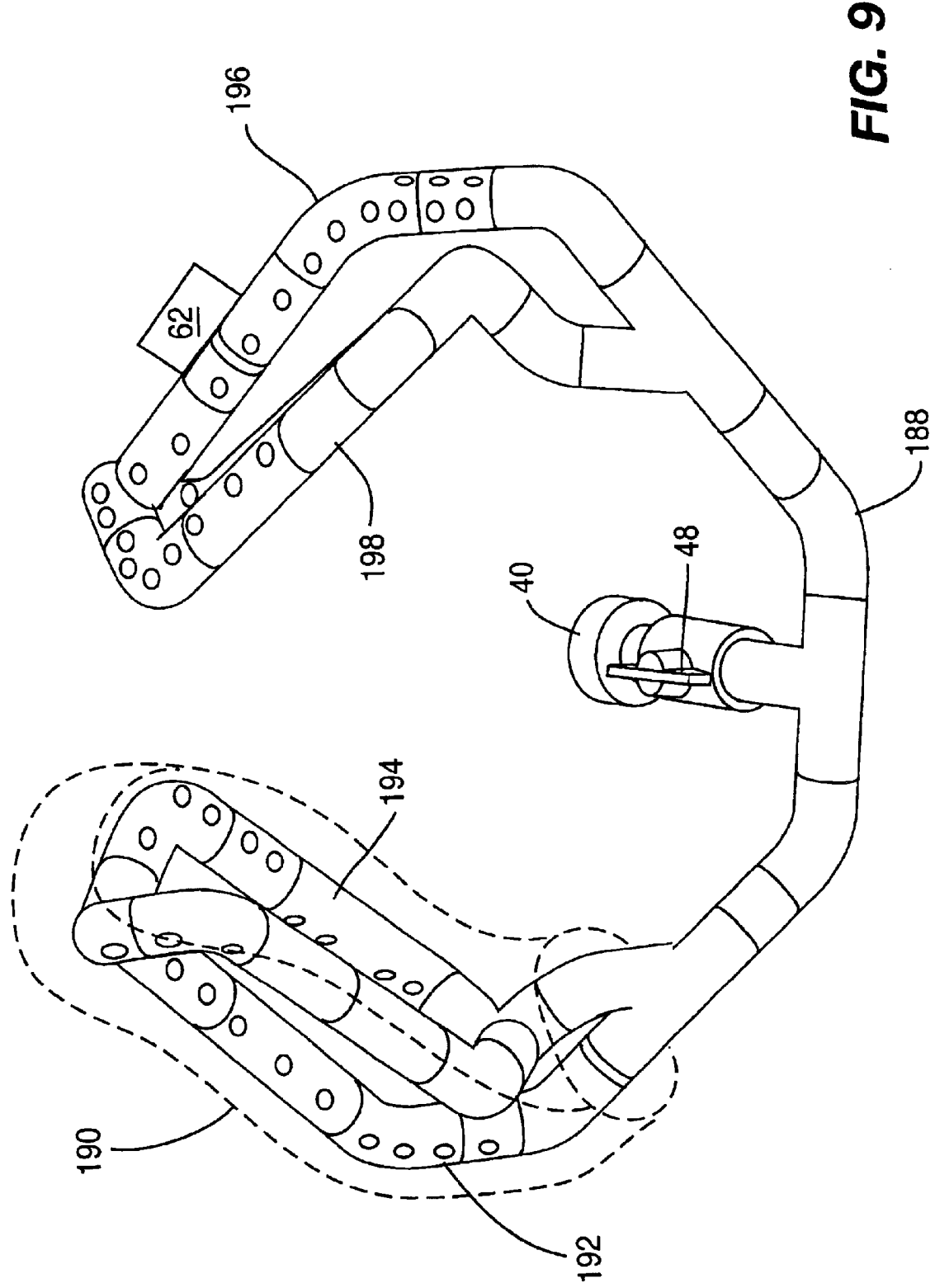
FIG. 9 is a perspective illustration of an elbow pad drying fixture.

FIGS. 7 and 9 show the inclusion of a deodorizing means 62. Such deodorizing means 62 can be utilized specifically in those situations where washing is not possible and only drying of sweat filled articles 10 is possible. In those situations it is best to maximize the amount of deodorizing of the articles 10 during drying thereof. As such, a deodorizing means 62 can be attached at various locations to the hanging conduit section 42 of any one of the drying fixtures 32 and in this manner reduce unwanted odors in the article 10 during drying thereof. Such deodorizing material can include any material commonly used for odor elimination such as non-toxic environmentally safe volcanic materials, charcoal odor absorbing filters or any other similar deodorizing material.

Figure 2:
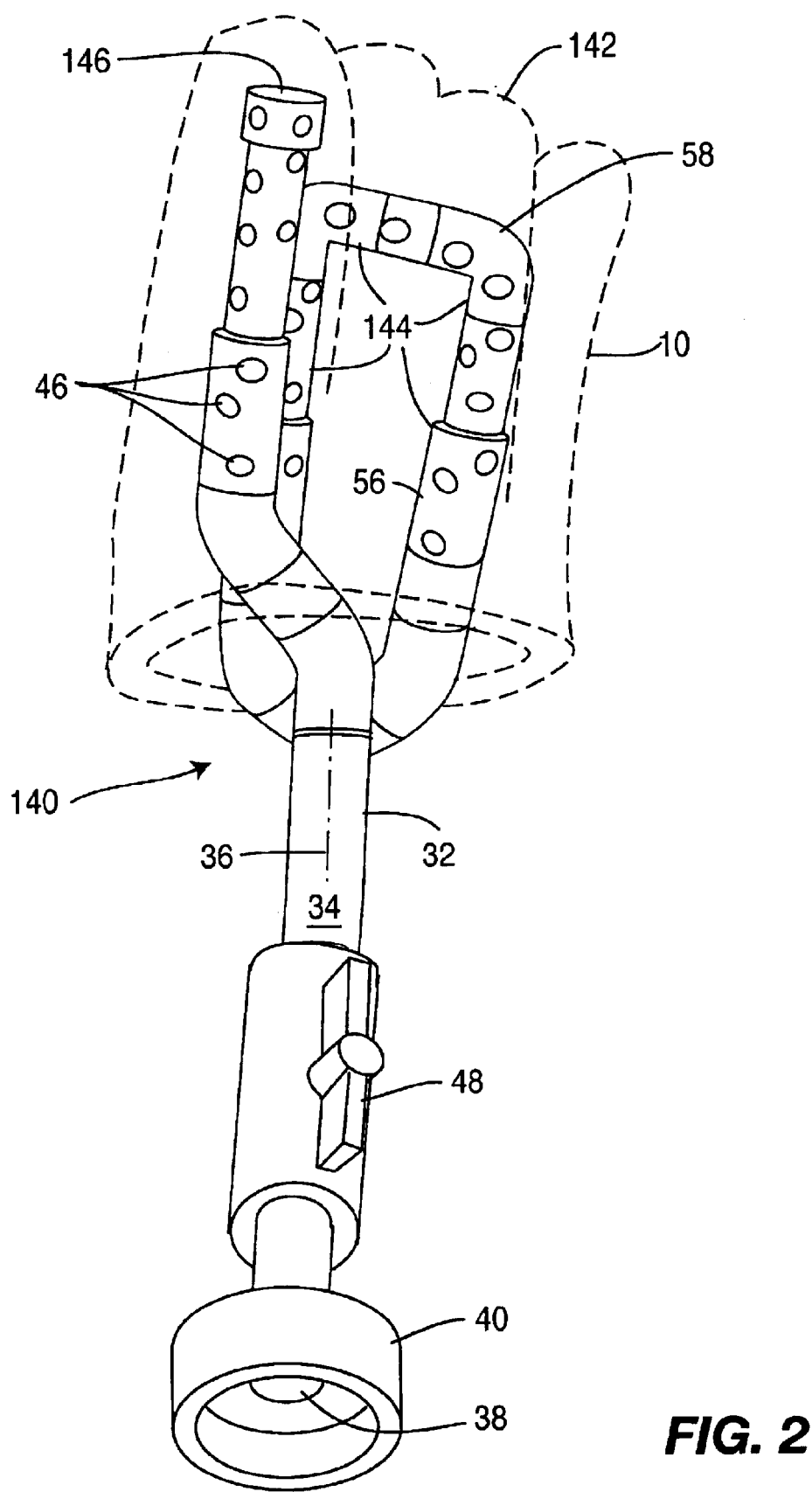
FIG. 2 is a perspective illustration of an embodiment of a glove drying fixture.

In FIG. 2 a particular embodiment of the drying fixture 32 is disclosed for the purpose of drying gloves. This glove fixture 140 is designed for the purpose of eliminating odors on hand coverings such as gloves or mittens 142. The glove or mitten 142 is shown in dotted outline surrounding the hanging section 42 of glove fixture 140. Glove fixture 140 includes a hand loop section 144 which is generally circular in shape and a thumb section 146 which is generally longitudinally in configuration. Preferably hand loop section 144 and thumb section 146 are positioned adjacent to one another to facilitate placement of a glove or other hand covering thereupon for enhancing drying thereof.

Figure 3:
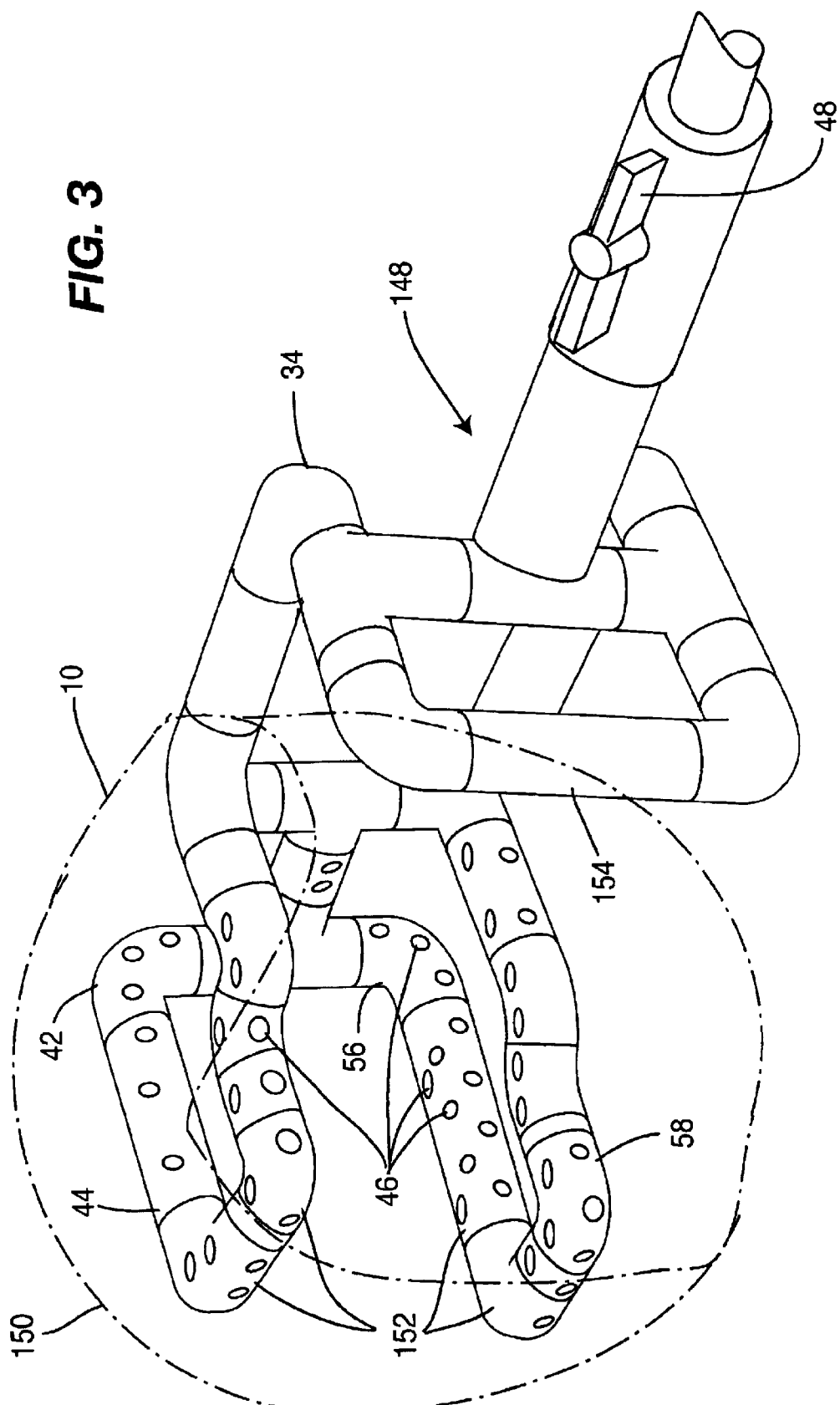
FIG. 3 is a perspective illustration of a headgear drying fixture.

FIG. 3 shows an embodiment of a helmet or headgear drying fixture 148 of the present invention which is designed specifically for the purpose of drying a helmet 150 or other headgear in dotted outline surrounding helmet fixture 148. The helmet fixture 148 preferably includes a rounded head section 152 as well as a chin support section 154 defines in a plane immediately adjacent the rounded head section 152 to facilitate drying of headgear positioned thereupon. In the preferred embodiment of this design the rounded head section 152 will be defined in the hanging conduit section 42 whereas the chin support section 154 will be defined in the connecting conduit section 34. Thus chin support section 154 will not include any drying holes 46 therein but the rounded head section 152 will indeed include drying holes 46.

Figure 4:
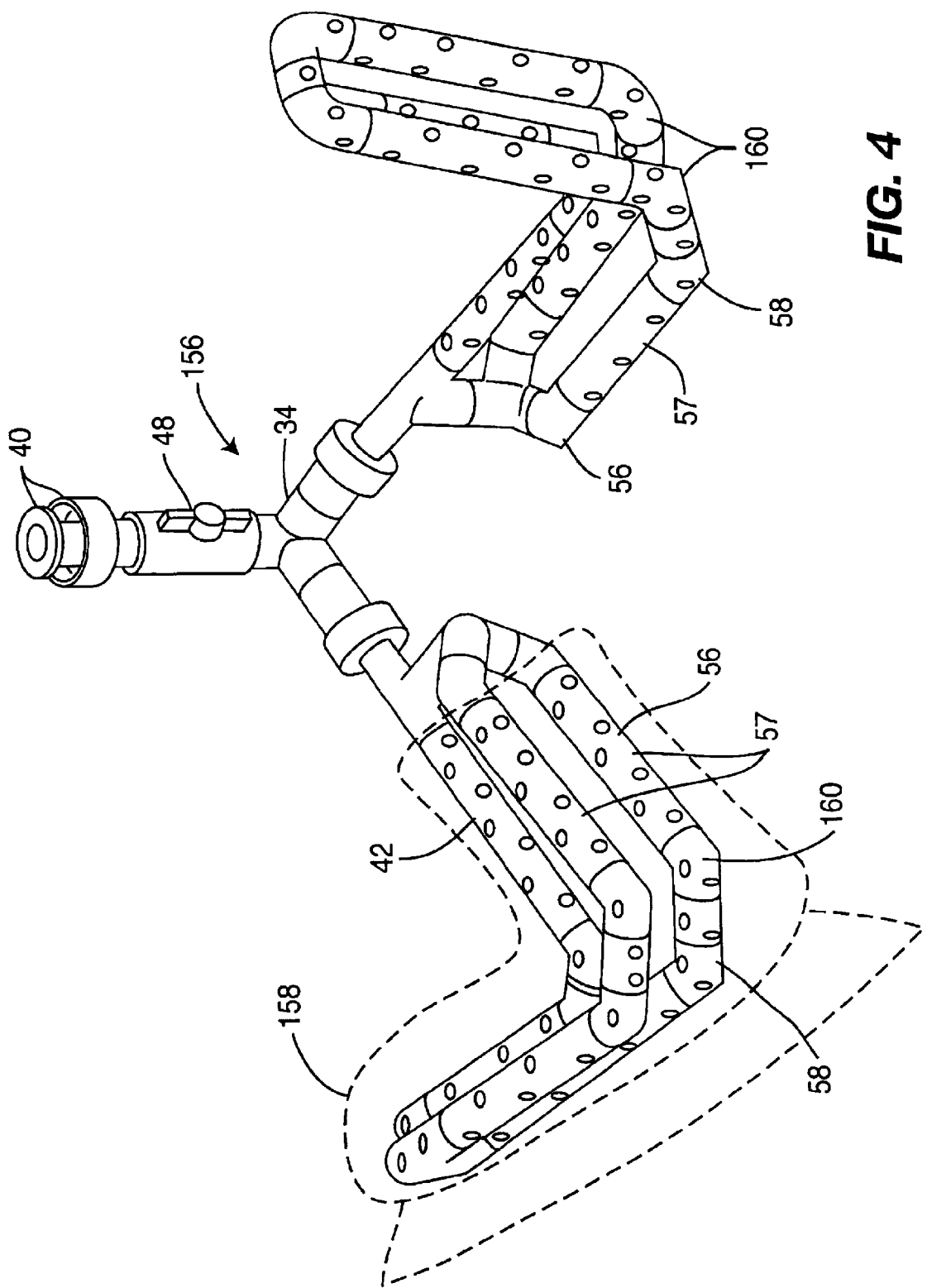
FIG. 4 is a perspective illustration of a footwear drying fixture.

A footwear fixture 156 is shown in FIG. 4. Footwear fixture 156 is adapted to dry various types of footwear most commonly being shoes, boots, cleats or skates 158. These footwear devices are shown in FIG. 4 in dotted outline as reference 158. The footwear fixture 156 preferably defines one or more L-shaped loop sections 160 which are designed to receive the general overall L-shape of one or more footwear items wherein the lower portion is the sole portion of the footwear and the part extending at approximately ninety degrees with respect thereto comprises the ankle portion thereof.

Figure 5:
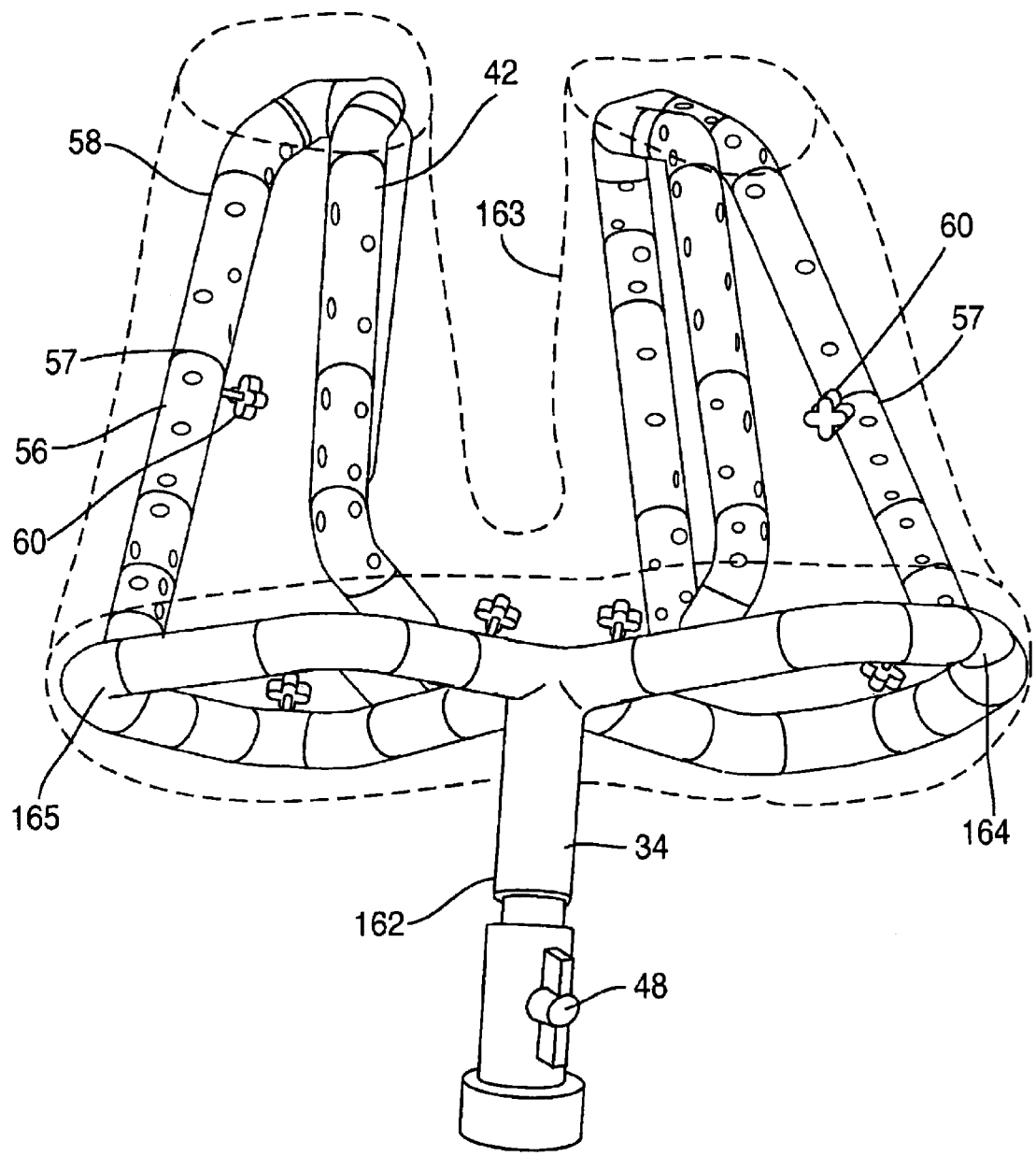
FIG. 5 is a perspective illustration of a long pants drying fixture.

A long pants fixture 162 is shown in FIG. 5. Long pants 163 are shown in dotted outline extending over the first pants section 164 and the second pants section 165 comprising the long pants fixture 162. These first and second pants sections are preferably positioned spatially apart and extending generally parallel to each other and are of a tapered cylindrical shape to facilitate placement of individual pant legs thereover for facilitating drying thereof.

Figure 6:
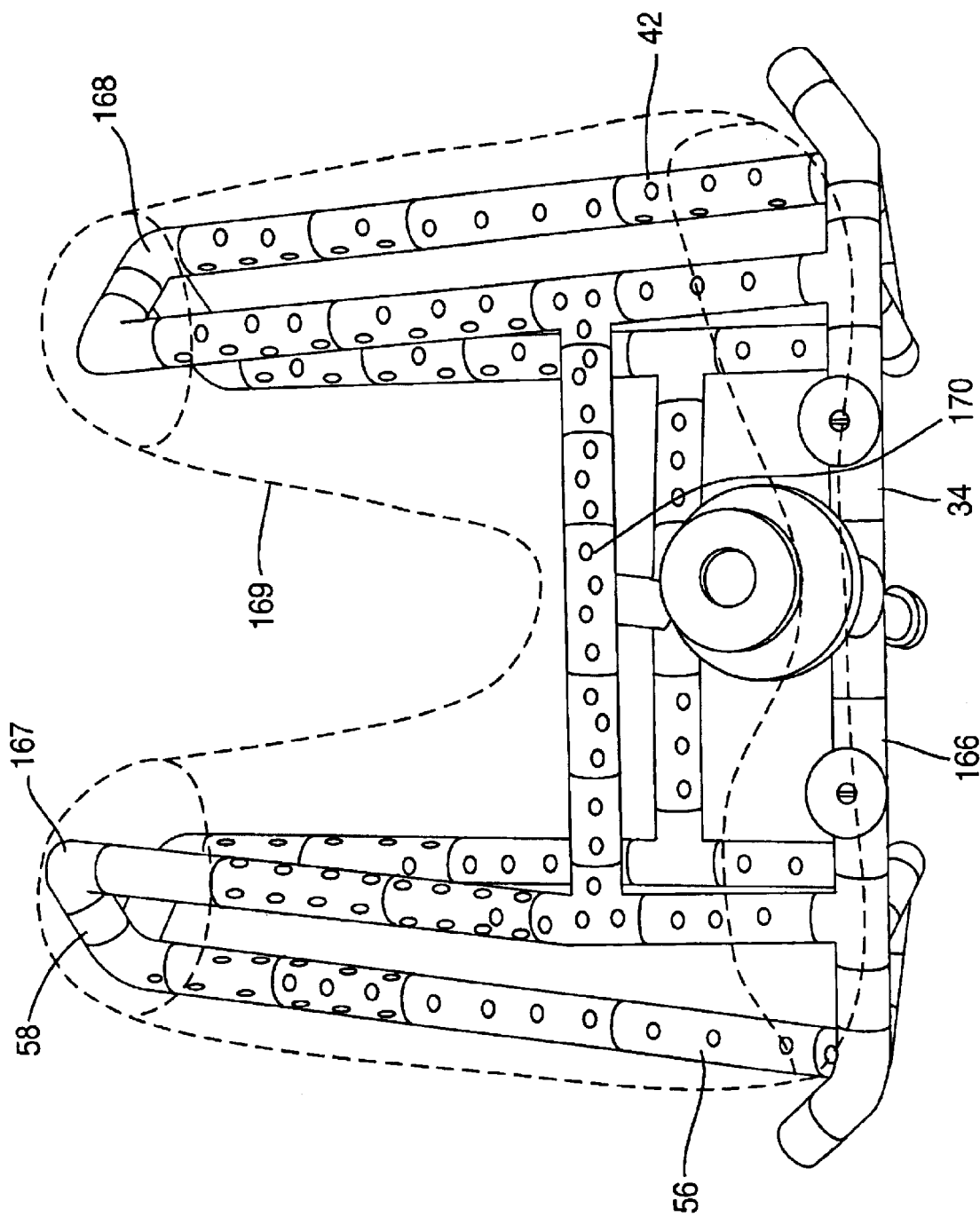
FIG. 6 is a perspective illustration of a protective cup shorts drying fixture.

FIG. 6 shows a cup shorts fixture 166. In many sports there are garments worn for holding supporters or cups between the legs of a user in the crotch area and these areas need to be dried significantly since they are the source of a significant amount of perspiration. As such, a specific cup shorts fixture 166 is included with a first leg section 167 and a second leg section 168 and a crotch cup section 170 extending therebetween. These are designed to hold cup shorts 169 over the first and second leg sections 167 and 168 and the crotch cup section 170 as shown in dotted outline on FIG. 6. Each of the pants sections generally include a tapered cylindrical shape somewhat shorter than the first and second pants sections 164 and 165 of the long pants fixture 162.

An upper body fixture 172 is shown in FIG. 7. This upper body fixture is designed to facilitate drying of a jersey or shirt or jacket or other upper body garment 173 shown in dotted outline extending over the upper body fixture 172 of FIG. 7. The upper body fixture 172 includes a rounded chest section 174 as well as a first arm section 176 extending outwardly and downwardly therefrom and a second arm section 178 extending outwardly and downwardly at a location opposite from the first arm section 176. In this manner a convenient means is provided for drying upper body coverings such as jersey, shirts, jackets, vests or other similar items.

Figure 8:
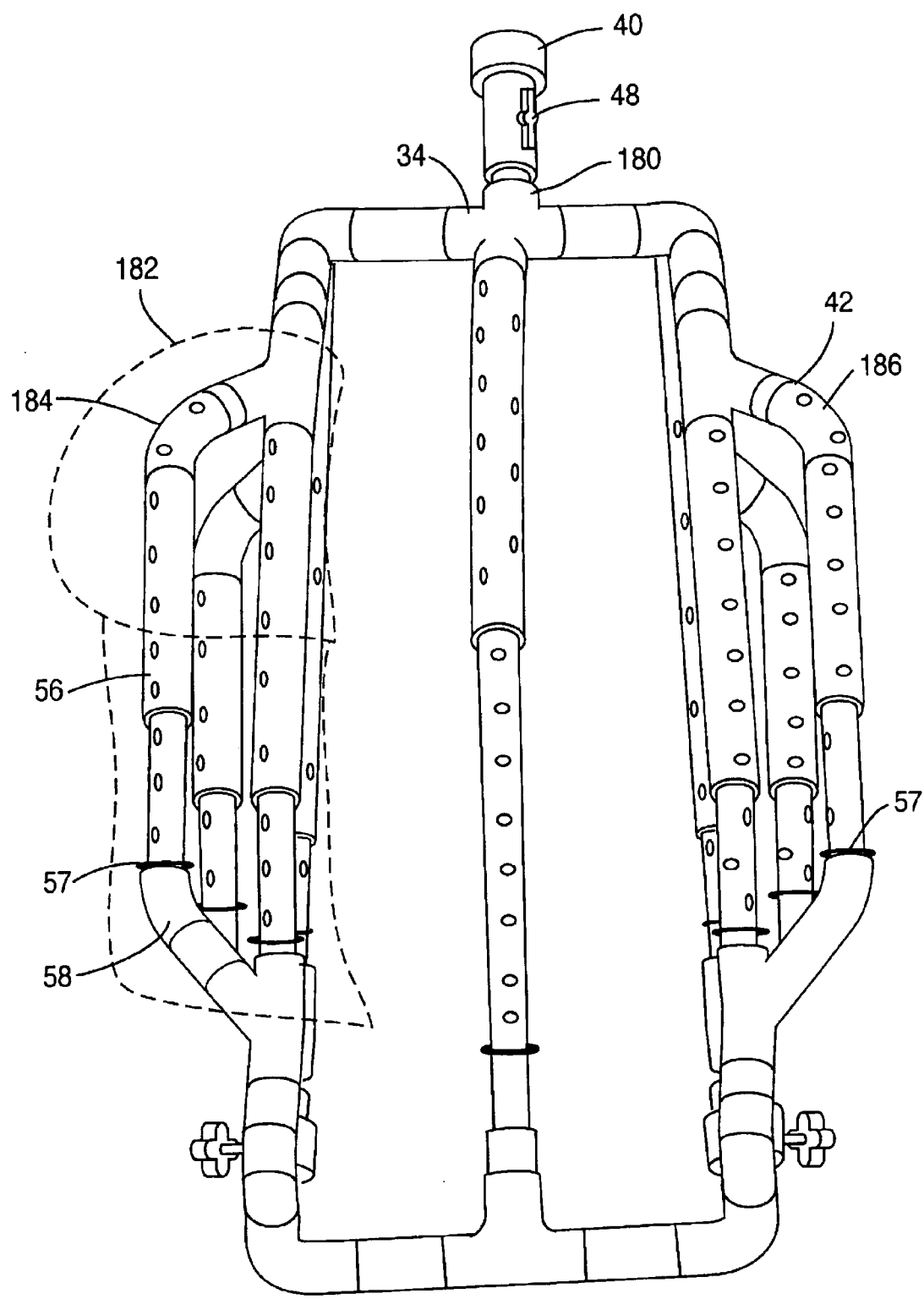
FIG. 8 is a perspective illustration of a leg protector drying fixture.

FIG. 8 shows a leg protector fixture 180. It includes a hanging conduit section which has a first longitudinal section 184 and a second longitudinal section 186 each shaped generally longitudinally cylindrically and oriented parallel with respect to one another to facilitate placement of a leg protection member thereupon for drying. Such leg protection members generally include shin guards or protective leg pads 182. These devices are shown in dotted outline extending over the first longitudinal section 184 defined in FIG. 8.

FIG. 9 shows an elbow pad fixture 188 wherein the hanging conduit section thereof includes a first upper arm section 192 and a first lower arm section 194 extending longitudinally and oriented at an obtuse angle with respect to one another. Similarly this elbow pad fixture 188 includes a second upper arm section 196 and a second lower arm section 198 extending longitudinally and oriented at an obtuse angle with respect to the second upper arm section 196 in order to facilitate positioning of elbow pads 190 thereupon to facilitate drying. Elbow pads are normally positioned at an obtuse angle with respect to one another and this is the reason for the angular relationship between the first upper arm section 192 and the first lower arm section 194 as well as the angular relationship between the second upper arm section 196 and the second lower arm section 198.

Figure 10:
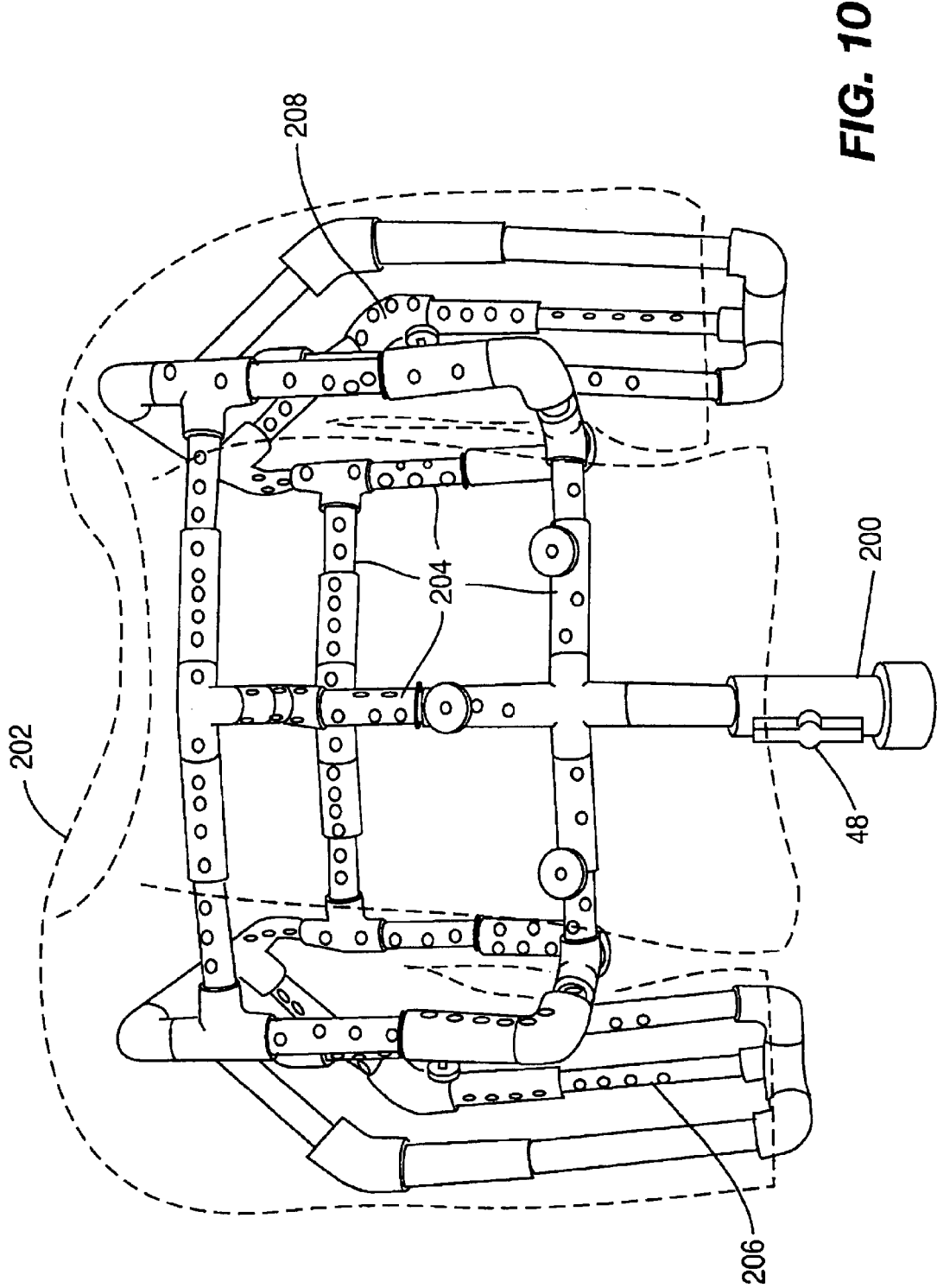
FIG. 10 is a perspective illustration of a chest and shoulder protection drying fixture.

FIG. 10 shows a chest protection fixture 200 designed specifically for the purpose of drying a chest protector or shoulder pad 202. These pads or protectors 202 are shown in dotted outline extending over the chest protection fixture 200 in FIG. 10. The chest protection fixture 200 includes a rectangular chest section 204 as well as a left arm section 206 extending outwardly and downwardly therefrom and a right arm section 208 also extending outwardly and downwardly therefrom oppositely positioned from left arm section 206. As such the chest protection fixture 200 of FIG. 10 provides a unique overall configuration for the drying of chest protectors and shoulder pads 202.

One of the major novel aspects of the present invention is in the configuration of the distributing manifold 22 of the present invention as shown best in FIG. 1. The distributing manifold 22 preferably includes a fixed manifold member 64 which defines a first manifold outlet 66 and a second manifold outlet 68 as well as a left fixed manifold exit aperture 70 and a right fixed manifold exit aperture 72. In the preferred configuration first and second manifold outlets 66 and 68 can be fixedly secured and immovable with respect to the overall configuration of the fixed manifold member 64. These manifold outlets 66 and 68 can pivot slightly if desired to provide variation in positioning thereof. They are shown in FIG. 1 extending forwardly from the fixed manifold member 64.

Additionally the distributing manifold 22 will include a left adjustable manifold member 74 and a right adjustable manifold member 76. Each of these manifolds is significantly adjustable through a continuum of different possible positions and orientations relative to the main conduit 14 for the purpose of varying the drying positions of the drying fixtures during operation of the blower 12. Thus it is preferably that the fixed manifold member 64 include fixedly positioned outlets such as 66 and 68 but also variably positionable outlets such as those defined in the left adjustable manifold member 74 and the right adjustable manifold member 76.

In particular the left adjustable manifold member 74 preferably will define a left linking adjustable conduit section 78. This section 78 is movably positionable preferably rotatably with respect to the left fixed manifold exit aperture 70.

A first left adjustable conduit section 82 is adjustably positionable with respect to the left linking adjustable conduit section 78 and a second left adjustable conduit section 84 is adjustable positionable with respect to the left linking adjustable conduit section 78. In this manner positioning of the conduit sections 82 and 84 vary relative to the left linking adjustable conduit section 78 and the fixed manifold member 64 provides an overall variability in positioning of the drying fixtures. A first left splitting conduit 86 is preferably positioned extending outwardly from the first left adjustable conduit section 82. The first left splitting conduit 86 will define a third manifold outlet 88 and a fourth manifold outlet 90 therewithin. Similarly the second left splitting conduit 92 will be in fluid flow communication with the second left adjustable conduit section 84 and extend outwardly therefrom to define therein the fifth manifold outlet 94 and the sixth manifold outlet 96. In this manner the left linking adjustable conduit 78 will include four separate manifold outlets 88, 90, 94 and 96 which are movable with respect to one another.

Also it is preferable that the first left adjustable conduit section 82 include a first left valve 112 therewithin which is capable of being moved to the closed position to prevent the flow of drying air therethrough to the third manifold outlet 88 and the fourth manifold outlet 90 if desired. This would be needed when the articles 10 to be dried positioned thereupon become fully dried and no longer need air supplied thereto or when those outlets are not being utilized for drying.

Similarly a second left valve 114 is preferably positioned within the second left adjustable conduit section 84 such as to selectively cause a cessation of air flow therethrough and prevent the movement of air to the second left splitting conduit 92 and the fifth manifold outlet 94 and sixth manifold outlet 96 defined therewithin.

In a similar manner the right adjustable manifold member 76 preferably can include a right linking adjustable conduit section 118 extending directly outwardly from the right fixed manifold exit aperture 72 of fixed manifold member 64. A first right adjustable conduit section 120 and a second right adjustable conduit section 122 will preferably each be connected to the right linking adjustable conduit section 118 at positions separate from one another and be in fluid flow communication therewith. Thus the first right adjustable conduit section 120 will extend outwardly from the right linking adjustable conduit section 118 at a first location and the second right adjustable conduit section 122 will extend outwardly therefrom at another non-adjacent position.

A first right splitting conduit 124 will extend outwardly from the first right adjustable conduit section 120 and will define a seventh manifold outlet 126 and an eighth manifold outlet 128 therewithin. In a similar manner a second right splitting conduit 130 will extend outwardly from the second right adjustable conduit section 122 to define a ninth manifold outlet 132 therein and a tenth manifold outlet 134 therewithin. In this manner the first right splitting conduit 124 will be separately movable and positionable from the second right splitting conduit 130 to vary the relative positioning of the sixth and seventh manifold outlets 126 and 128 from the ninth and tenth manifold outlets 132 and 134.

A first right valve 136 is preferably positioned within the first right adjustable conduit section 120 for controlling and possibly eliminating air flow to the seventh manifold outlet 126 and the eighth manifold outlet 128. In a similar manner a second right valve 138 can be positioned in the second right adjustable conduit section 122 for restricting or completely eliminating the flow of drying air to the ninth manifold outlet 132 and the tenth manifold outlet 134 defined by the second right splitting conduit 130. As such these valves can provide full flow or no flow or restricted flow as desired by manipulation of the valving means contained therewithin.

Thus, in the particular embodiment shown in FIG. 1, the first and second manifold outlets 66 and 68 can be fixedly mounted within the fixed manifold 64. On the other hand the other outlets will all be movably positioned. In particular, third manifold outlet 88 and fourth manifold outlet 90 are defined by the first left splitting conduit 86 and are movable therewith. In a similar manner the fifth manifold outlet 94 and the sixth manifold outlet 96 are defined in the second left splitting conduit 92 and are adjustably positionable therewith. In a similar manner the seventh manifold outlet 126 and the eighth manifold outlet 128 are movably positioned along with the first right splitting conduit 124. Similarly the ninth manifold outlet 132 and the tenth manifold outlet 134 are movably positioned along with the second right splitting conduit 130. Each of these ten manifold outlets include mounted thereadjacent a respective manifold attachment device. As such, ten manifold attachment means are included. These are shown by reference numerals 101 through 110. First manifold attachment device 101 and second manifold attachment device 102 are secured with respect to the first manifold outlet 66 and the second manifold outlet 68 respectively. Similarly third manifold attachment device 103 and fourth manifold attachment device 104 are secured to the third and fourth manifold outlets 88 and 90. The fifth manifold attachment device 105 and the sixth manifold attachment device 106 are secured to the fifth and sixth manifold outlets 94 and 96.

Furthermore the seventh and eighth manifold attachment devices 107 and 108 are secured respectively to the seventh and eighth manifold outlets 126 and 128 and finally the ninth and tenth manifold attachment means 109 and 110 are secured to the ninth and tenth manifold outlets 132 and 134 respectively.

In this manner each manifold outlet includes a manifold attachment means mounted thereadjacent or therewithin that will facilitate securement thereof with respect to any one of the two to ten or more drying fixtures 32 of the present invention because they are securable with respect to the fixture attachment means 40 thereof. Thus each drying fixture 32 will include a fixture attachment means 40 attachable to any one of the ten or more individual manifold attachment devices 101 to 110 as shown in this embodiment. It should be appreciated that distributing manifold 22 can define any number of manifold outlets and manifold attachment means and that the present invention can be provided with any number of different drying fixtures 32 having variable configurations for drying different types, shapes and sizes of articles 10.

It should also be appreciated that the left adjustable manifold member 74 can be removed from securement with respect to the left fixed manifold aperture 70 and this aperture closed by the securement of a left capping means 98 extending thereover. In a similar manner a right capping means 99 can be positioned extending over the right fixed manifold exit aperture 72 after removal of the right adjustable manifold 76 therefrom in order to restrict flow therethrough. Thus each of the adjustable manifold members 74 and 76 can selectively be utilized or removed and the opening to which they have been connected can be closed by securement with respect to one or more capping means 98 and/or 99. This provides further versatility to the apparatus of the present invention.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. A portable apparatus for drying articles comprising:
    A. a blower means;
    B. a main conduit defining a main duct means extending therewithin capable carrying air flow therethrough, said main conduit also defining a main conduit inlet means and a main conduit outlet means each being in fluid flow communication with respect to said main duct means to facilitate air flowing into said main duct means through said main conduit inlet means and outwardly from said main duct means through said main conduit outlet means, said main conduit inlet means being operatively attached with respect to said blower means to receive air flow therefrom;
    C. a distributing manifold defining a manifold duct means extending therewithin and further defining a manifold inlet means in fluid flow communication with respect to said manifold duct means for facilitating air flow therebetween, said manifold inlet means being operatively attached to said main conduit outlet means to receive air exiting therefrom, said distributing manifold defining a plurality of manifold outlet means therewithin;
    D. a plurality of manifold attachment means with one mounted within each of said manifold outlet means to facilitate detachably securement thereto;
    E. a plurality of drying fixture means each being detachably securable with respect to any one of said manifold attachment means for receiving of air flow therefrom, each of said drying fixture providing a means for drying articles of various different specific shapes, each of said drying fixture means including:
        (1) a connecting conduit section defining a connecting section duct means extending therethrough for carrying air flow, said connecting conduit section further defining a drying fixture opening means therewithin in fluid flow communication with respect to said connecting section duct means;
        (2) a fixture attachment means mounted on said connecting conduit section adjacent said drying fixture opening means and being selectively securable with respect to any one of said manifold attachment means to detachably mount one of said drying fixture means with respect to said distributing manifold to allow fluid flow communication between said distributing manifold outlet means and said drying fixture opening means for facilitating air flow into said connecting section duct means of said drying fixture means to facilitate drying therewith;
        (3) a hanging conduit section defining a hanging section duct means extending therethrough, said hanging section duct means in direct fluid flow communication with respect to said connecting section duct means, said hanging conduit section defining a plurality of drying hole means therein which are in fluid flow communication with respect to said hanging section duct means for dispensing air outwardly therefrom for drying of an article positioned thereadjacent, said hanging conduit section adapted to receive an article detachably held thereadjacent to facilitate drying thereof as air flows outwardly therefrom through said drying hole means defined therewithin; and
        (4) a fixture valve means positioned within said connecting conduit section of said drying fixture means and extending thereacross to control air flow through said connecting section duct means.

2. A portable apparatus for drying of articles as defined in claim 1 wherein said blower means comprises a heated blower means for supplying of heated air to said main conduit to facilitate drying.

3. A portable apparatus for drying of articles as defined in claim 1 wherein said main conduit further defines a scenting chamber means therewithin for selectively holding of scenting material therewithin for scenting of air passing through said main duct means.

4. A portable apparatus for drying of articles as defined in claim 3 wherein said main conduit means further defines an access opening means therein to provide access to said scenting chamber means for maintenance therewithin, said main conduit means further defining an access door means movable between a closed position extending across said access opening means for sealing thereof and an opened position to provide access through said access opening means into said scenting chamber means.

5. A portable apparatus for drying of articles as defined in claim 1 wherein each of said fixture valve means is movable to a completely opened position to allow full air flow through said connecting conduit section of said drying fixture means and to a completely closed position to prevent any air flow through said connecting conduit section of said drying fixture means and to any intermediate position therebetween to restrict air flow through said connecting conduit section of said drying fixture means.

6. A portable apparatus for drying of articles as defined in claim 1 wherein said hanging conduit section of each of said drying fixture means is of an adjustable size and includes:
  A. a first hanging member defining a portion of said hanging section duct means therewith, said first hanging member defining a plurality of said drying hole means therewithin; and
  B. a second hanging member defining a portion of said hanging section duct means therewith, said first hanging member defining a plurality of said drying hole means therewithin, said second hanging member positioned in telescoping engagement with respect to said first hanging member and movable in telescoping manner with respect thereto to vary the overall dimensions of said hanging conduit section of said drying fixture means for facilitating usage thereof with articles of various sizes for drying adjacently positioned thereupon.

7. A portable apparatus for drying of articles as defined in claim 6 wherein said hanging conduit section includes a set screw means engageable with respect to said first hanging member and said second hanging member for selectively preventing telescoping movement therebetween when fully engaged while allowing telescoping movement therebetween when disengaged.

8. A portable apparatus for drying of articles as defined in claim 1 wherein said drying fixture means includes a deodorizing means attachable with respect to said drying fixture means to facilitate deodorizing of articles while drying positioned thereupon.

9. A portable apparatus for drying of articles as defined in claim 1 wherein said distributing manifold includes:
  A. a fixed manifold member secured with respect to said main conduit and having a fixed configuration, said fixed manifold member defining said manifold inlet means, said manifold inlet means being positioned by said fixed manifold member in fluid flow communication with respect to said main conduit outlet means to facilitate air flow therebetween, said fixed manifold member defining a first manifold outlet and a second manifold outlet therein, said fixed manifold member also defining a left fixed manifold exit aperture and a right fixed manifold exit aperture therewithin;
  B. a left adjustable manifold member detachably secured with respect to said left fixed manifold exit aperture for receiving air flow therefrom, said left adjustable manifold member having an adjustable configuration; and
  C. a right adjustable manifold member detachably secured with respect to said right fixed manifold exit aperture for receiving air flow therefrom, said right adjustable manifold member having an adjustable configuration.

10. A portable apparatus for drying of articles as defined in claim 9 further comprising a first manifold attachment means positioned within said first manifold outlet to selectively facilitate securement of a drying fixture means with respect thereto and further comprising a second manifold attachment means positioned within said second manifold outlet to selectively facilitate securement of a drying fixture means with respect thereto.

11. A portable apparatus for drying of articles as defined in claim 10 wherein said left adjustable manifold member comprises:
  A. a left linking adjustable conduit section detachably secured with respect to said left fixed manifold exit aperture for receiving air flow therefrom; and
  B. a first left adjustable conduit section detachably connected with respect to said left linking adjustable conduit section to receive air flow therefrom;
  C. a second left adjustable conduit section also being detachably connected with respect to said left linking adjustable conduit section to receive air flow therefrom;
  D. a first left splitting conduit connected with respect to said first left adjustable conduit section to receive air flow therefrom, said first left splitting conduit defining a third manifold outlet and a fourth manifold outlet therewithin; and
  E. a second left splitting conduit connected with respect to said second left adjustable conduit section to receive air flow therefrom, said second left splitting conduit defining a fifth manifold outlet and a sixth manifold outlet therewithin.

12. A portable apparatus for drying of articles as defined in claim 11 further comprising a third manifold attachment means positioned within said third manifold outlet to selectively facilitate securement of a drying fixture means with respect thereto and further comprising a fourth manifold attachment means positioned within said fourth manifold outlet to selectively facilitate securement of a drying fixture means with respect thereto and further comprising a fifth manifold attachment means positioned within said fifth manifold outlet to selectively facilitate securement of a drying fixture means with respect thereto and further comprising a sixth manifold attachment means positioned within said sixth manifold outlet to selectively facilitate securement of a drying fixture means with respect thereto.

13. A portable apparatus for drying of articles as defined in claim 12 further comprising a first left valve means positioned within said first left adjustable conduit section to control air flow therethrough to said third manifold outlet and said fourth manifold outlet and further comprising a second left valve means positioned within said second left adjustable conduit section to control air flow therethrough to said fifth manifold outlet and said sixth manifold outlet.

14. A portable apparatus for drying of articles as defined in claim 13 wherein said right adjustable manifold member comprises:
  A. a right linking adjustable conduit section detachably secured with respect to said right fixed manifold exit aperture for receiving air flow therefrom; and
  B. a first right adjustable conduit section detachably connected with respect to said right linking adjustable conduit section to receive air flow therefrom;
  C. a second right adjustable conduit section also being detachably connected with respect to said right linking adjustable conduit section to receive air flow therefrom;
  D. a first right splitting conduit connected with respect to said first right adjustable conduit section to receive air flow therefrom, said first right splitting conduit defining a seventh manifold outlet and a eighth manifold outlet therewithin; and
  E. a second right splitting conduit connected with respect to said second right adjustable conduit section to receive air flow therefrom, said second right splitting conduit defining a ninth manifold outlet and a tenth manifold outlet therewithin.

15. A portable apparatus for drying of articles as defined in claim 14 further comprising a seventh manifold attachment means positioned within said seventh manifold outlet to selectively facilitate securement of a drying fixture means with respect thereto and further comprising a eighth manifold attachment means positioned within said eighth manifold outlet to selectively facilitate securement of a drying fixture means with respect thereto and further comprising a ninth manifold attachment means positioned within said ninth manifold outlet to selectively facilitate securement of a drying fixture means with respect thereto and further comprising a tenth manifold attachment means positioned within said tenth manifold outlet to selectively facilitate securement of a drying fixture means with respect thereto.

16. A portable apparatus for drying of articles as defined in claim 15 further comprising a first right valve means positioned within said first right adjustable conduit section to control air flow therethrough to said seventh manifold outlet and said eighth manifold outlet and further comprising a second right valve means positioned within said second right adjustable conduit section to control air flow therethrough to said ninth manifold outlet and said tenth manifold outlet.

17. A portable apparatus for drying of articles as defined in claim 9 further comprising a left capping means detachably securable with respect to said left fixed manifold exit aperture means for selectively closing same and preventing air flow therethrough and further comprising a right capping means detachably securable with respect to said right fixed manifold exit aperture means for selectively closing same and preventing air flow therethrough.

18. A portable apparatus for drying of articles as defined in claim 1 wherein one of said plurality of drying fixture means comprises a glove fixture wherein said hanging conduit section thereof includes a hand loop section being generally circular in shape and a thumb section being generally longitudinally in shape which are positioned adjacent to one another to facilitate placement of a glove thereupon for enhancing drying thereof during operation of said blower means.

19. A portable apparatus for drying of articles as defined in claim 1 wherein one of said plurality of drying fixture means includes a headgear fixture wherein said hanging conduit section thereof includes a rounded head section and wherein said connecting conduit section defines a chin support section defined in a plane immediately adjacent said rounded head section to facilitating placement of headgear thereupon for enhancing drying thereof during operation of said blower means.

20. A portable apparatus for drying of articles as defined in claim 1 wherein one of said plurality of drying fixture means comprises a footwear fixture wherein said hanging conduit section thereof includes a plurality of L-shaped loop section to facilitate placement of at least one footwear item thereupon for enhancing drying thereof during operation of said blower means.

21. A portable apparatus for drying of articles as defined in claim 1 wherein one of said plurality of drying fixture means comprises a long pants fixture wherein said hanging conduit section thereof includes a first pants section and a second pants section positioned spatially apart and extending generally parallel to one another, said first pants section and said second pants section each being of a tapered cylindrical shape to facilitate placement of a long pants thereupon for enhancing drying thereof during operation of said blower means.

22. A portable apparatus for drying of articles as defined in claim 1 wherein one of said plurality of drying fixture means comprises a cup shorts fixture wherein said hanging conduit section thereof includes a first short pants section and a second short pants section extending generally parallel to one another and each being of a tapered cylindrical shape, said cup shorts fixture further including a crotch cup section extending laterally between said first short pants section and said second short pants section to facilitate drying, said cup shorts fixture adapted to facilitate placement of cup short pants with a crotch cup area upon said first short pants section and upon said second short pants section with the crotch area thereof extending over said crotch cup section for enhancing drying thereof during operation of said blower means.

23. A portable apparatus for drying of articles as defined in claim 1 wherein one of said plurality of drying fixture means comprises a upper body fixture wherein said hanging conduit section thereof includes a rounded chest section and a first arm section extending outwardly and downwardly therefrom and a second arm section extending outwardly and downwardly oppositely from said first arm section to facilitate placement of an upper body garment thereupon for enhancing drying thereof during operation of said blower means.

24. A portable apparatus for drying of articles as defined in claim 1 wherein one of said plurality of drying fixture means comprises a leg protector fixture wherein said hanging conduit section thereof includes a first longitudinal section and a second longitudinal section each shaped generally longitudinally cylindrically and oriented parallel with respect to one another to facilitate placement of at least one leg protecting member thereupon for enhancing drying thereof during operation of said blower means.

25. A portable apparatus for drying of articles as defined in claim 1 wherein one of said plurality of drying fixture means comprises an elbow pad fixture wherein said hanging conduit section thereof includes an first upper arm section and a first lower arm section extending longitudinally and oriented at an obtuse angle with respect to one another and wherein said hanging conduit section further includes an second upper arm section and a second lower arm section extending longitudinally and oriented at an obtuse angle with respect to one another in order to facilitate positioning of a pair of elbow pads adjacent to one another on said hanging conduit section for enhancing drying thereof during operation of said blower means.

26. A portable apparatus for drying of articles as defined in claim 1 wherein one of said plurality of drying fixture means comprises a chest protection fixture wherein said hanging conduit section thereof includes a rectangular chest section and a left arm section extending outwardly and downwardly therefrom and a right arm section extending outwardly and downwardly oppositely from said left arm section to facilitate placement of a chest protection apparatus thereupon for enhancing drying thereof during operation of said blower means.

27. A portable apparatus for drying articles comprising:
A. a blower means included a heating means to facilitate supplying of heated air for warming and drying;
B. a main conduit defining a main duct means extending therewithin capable carrying air flow therethrough, said main conduit also defining a main conduit inlet means and a main conduit outlet means each being in fluid flow communication with respect to said main duct means to facilitate air flowing into said main duct means through said main conduit inlet means and outwardly from said main duct means through said main conduit outlet means, said main conduit inlet means being operatively attached with respect to said blower means to receive air flow therefrom, said main conduit further defining a scenting chamber means therewithin for selectively holding of scenting material therewithin for scenting of air passing through said main duct means;

C. a distributing manifold defining a manifold duct means extending therewithin and further defining a manifold inlet means in fluid flow communication with respect to said manifold duct means for facilitating air flow therebetween, said manifold inlet means being operatively attached to said main conduit outlet means to receive air exiting therefrom, said distributing manifold defining a plurality of manifold outlet means therewithin;

D. a plurality of manifold attachment means with one mounted within each of said manifold outlet means to facilitate detachably securement thereto;

E. a plurality of drying fixture means each being detachably securable with respect to any one of said manifold attachment means for receiving of air flow therefrom, each of said drying fixture providing a means for drying articles of various different specific shapes, each of said drying fixture means including:

(1) a connecting conduit section defining a connecting section duct means extending therethrough for carrying air flow, said connecting conduit section further defining a drying fixture opening means therewithin in fluid flow communication with respect to said connecting section duct means;

(2) a fixture attachment means mounted on said connecting conduit section adjacent said drying fixture opening means and being selectively securable with respect to any one of said manifold attachment means to detachably mount one of said drying fixture means with respect to said distributing manifold to allow fluid flow communication between said distributing manifold outlet means and said drying fixture opening means for facilitating air flow into said connecting section duct means of said drying fixture means to facilitate drying therewith;

(3) a hanging conduit section defining a hanging section duct means extending therethrough, said hanging section duct means in direct fluid flow communication with respect to said connecting section duct means, said hanging conduit section defining a plurality of drying hole means therein which are in fluid flow communication with respect to said hanging section duct means for dispensing air outwardly therefrom for drying of an article positioned thereadjacent, said hanging conduit section adapted to receive an article detachably held thereadjacent to facilitate drying thereof as air flows outwardly therefrom through said drying hole means defined therewithin, said hanging conduit section of each of said drying fixture means being of adjustable size and including:

(a) a first hanging member defining a portion of said hanging section duct means therewith, said first hanging member defining a plurality of said drying hole means therewithin;

(b) a second hanging member defining a portion of said hanging section duct means therewith, said first hanging member defining a plurality of said drying hole means therewithin, said second hanging member positioned in telescoping engagement with respect to said first hanging member and movable in telescopic manner with respect thereto to vary the overall dimensions of said hanging conduit section of said drying fixture means for facilitating usage thereof with articles of various sizes for drying adjacently positioned thereupon; and (4) a fixture valve means positioned within said connecting conduit section of each of said drying fixture means and extending thereacross to control air flow through said connecting section duct means, each of said fixture valve means being movable to a completely opened position to allow full air flow through said connecting conduit section of said drying fixture means and to a completely closed position to prevent any air flow through said connecting conduit section of said drying fixture means and to any intermediate position therebetween to restrict air flow through said connecting conduit section of said drying fixture means.

28. A portable apparatus for drying articles comprising:

A. a blower means included a heating means to facilitate supplying of heated air for warming and drying;

B. a main conduit defining a main duct means extending therewithin capable carrying air flow therethrough, said main conduit also defining a main conduit inlet means and a main conduit outlet means each being in fluid flow communication with respect to said main duct means to facilitate air flowing into said main duct means through said main conduit inlet means and outwardly from said main duct means through said main conduit outlet means, said main conduit inlet means being operatively attached with respect to said blower means to receive air flow therefrom, said main conduit further defining a scenting chamber means therewithin for selectively holding of scenting material therewithin for scenting of air passing through said main duct means, said main conduit means further defining an access opening means therein to provide access to said scenting chamber means for maintenance therewithin, said main conduit means further defining an access door means movable between a closed position extending across said access opening means for sealing thereof and an opened position to provide access through said access opening means into said scenting chamber means;

C. a distributing manifold defining a manifold duct means extending therewithin and further defining a manifold inlet means in fluid flow communication with respect to said manifold duct means for facilitating air flow therebetween, said manifold inlet means being operatively attached to said main conduit outlet means to receive air exiting therefrom, said distributing manifold defining a plurality of manifold outlet means therewithin, said distributing manifold further including;

(1) a fixed manifold member secured with respect to said main conduit and having a fixed configuration, said fixed manifold member defining said manifold inlet means, said manifold inlet means being positioned by said fixed manifold member in fluid flow communication with respect to said main conduit outlet means to facilitate air flow therebetween, said fixed manifold member defining a first manifold outlet and a second manifold outlet therein, said fixed manifold member also defining a left fixed manifold exit aperture and a right fixed manifold exit aperture therewithin;

(2) a left adjustable manifold member detachably securable with respect to said left fixed manifold exit aperture for receiving air flow therefrom, said left adjustable manifold member having an adjustable configuration, said left adjustable manifold member comprising:
  (a) a left linking adjustable conduit section detachably secured with respect to said left fixed manifold exit aperture for receiving air flow therefrom;
  (b) a first left adjustable conduit section detachably connected with respect to said left linking adjustable conduit section to receive air flow therefrom;
  (c) a second left adjustable conduit section also being detachably connected with respect to said left linking adjustable conduit section to receive air flow therefrom;
  (d) a first left splitting conduit connected with respect to said first left adjustable conduit section to receive air flow therefrom, said first left splitting conduit defining a third manifold outlet and a fourth manifold outlet therewithin; and
  (e) a second left splitting conduit connected with respect to said second left adjustable conduit section to receive air flow therefrom, said second left splitting conduit defining a fifth manifold outlet and a sixth manifold outlet therewithin;
  (f) a first left valve means positioned within said first left adjustable conduit section to control air flow therethrough to said third manifold outlet and said fourth manifold outlet
  (g) a second left valve means positioned within said second left adjustable conduit section to control air flow therethrough to said fifth manifold outlet and said sixth manifold outlet;
(3) a right adjustable manifold member detachably securable with respect to said right fixed manifold exit aperture for receiving air flow therefrom, said right adjustable manifold member having an adjustable configuration, said right adjustable manifold member comprising:
  (a) a right linking adjustable conduit section detachably secured with respect to said right fixed manifold exit aperture for receiving air flow therefrom;
  (b) a first right adjustable conduit section detachably connected with respect to said right linking adjustable conduit section to receive air flow therefrom;
  (c) a second right adjustable conduit section also being detachably connected with respect to said right linking adjustable conduit section to receive air flow therefrom;
  (d) a first right splitting conduit connected with respect to said first right adjustable conduit section to receive air flow therefrom, said first right splitting conduit defining a seventh manifold outlet and a eighth manifold outlet therewithin; and
  (e) a second right splitting conduit connected with respect to said second right adjustable conduit section to receive air flow therefrom, said second right splitting conduit defining a ninth manifold outlet and a tenth manifold outlet therewithin;
  (f) a first right valve means positioned within said first right adjustable conduit section to control air flow therethrough to said seventh manifold outlet and said eighth manifold outlet;
  (g) a second right valve means positioned within said second right adjustable conduit section to control air flow therethrough to said ninth manifold outlet and said tenth manifold outlet;

D. a plurality of manifold attachment means including:
  (1) a first manifold attachment means positioned within said first manifold outlet to selectively facilitate securement with respect thereto;
  (2) a second manifold attachment means positioned within said second manifold outlet to selectively facilitate securement with respect thereto;
  (3) a third manifold attachment means positioned within said third manifold outlet to selectively facilitate securement with respect thereto;
  (4) a fourth manifold attachment means positioned within said fourth manifold outlet to selectively facilitate securement with respect thereto;
  (5) a fifth manifold attachment means positioned within said fifth manifold outlet to selectively facilitate securement with respect thereto;
  (6) a sixth manifold attachment means positioned within said sixth manifold outlet to selectively facilitate securement with respect thereto;
  (7) a seventh manifold attachment means positioned within said seventh manifold outlet to selectively facilitate securement with respect thereto;
  (8) a eighth manifold attachment means positioned within said eighth manifold outlet to selectively facilitate securement with respect thereto;
  (9) a ninth manifold attachment means positioned within said ninth manifold outlet to selectively facilitate securement with respect thereto;
  (10) a tenth manifold attachment means positioned within said tenth manifold outlet to selectively facilitate securement with respect thereto;
E. a plurality of drying fixture means each being detachably securable with respect to any one of said manifold attachment means for receiving of air flow therefrom, each of said drying fixture providing a means for drying articles of various different specific shapes, each of said drying fixture means including:
  (1) a connecting conduit section defining a connecting section duct means extending therethrough for carrying air flow, said connecting conduit section further defining a drying fixture opening means therewithin in fluid flow communication with respect to said connecting section duct means;
  (2) a fixture attachment means mounted on said connecting conduit section adjacent said drying fixture opening means and being selectively securable with respect to any one of said manifold attachment means to detachably mount one of said drying fixture means with respect to said distributing manifold to allow fluid flow communication between said distributing manifold outlet means and said drying fixture opening means for facilitating air flow into said connecting section duct means of said drying fixture means to facilitate drying therewith;
  (3) a hanging conduit section defining a hanging section duct means extending therethrough, said hanging section duct means in direct fluid flow communication with respect to said connecting section duct means, said hanging conduit section defining a plurality of drying hole means therein which are in fluid flow communication with respect to said hanging section duct means for dispensing air outwardly therefrom for drying of an article positioned thereadjacent, said hanging conduit section adapted to receive an article detachably held thereadjacent to facilitate drying thereof as air flows outwardly therefrom through said drying hole means defined therewithin, said hanging conduit section of each of said drying fixture means being of adjustable size and including:
(a) a first hanging member defining a portion of said hanging section duct means therewith, said first hanging member defining a plurality of said drying hole means therewithin;
(b) a second hanging member defining a portion of said hanging section duct means therewith, said first hanging member defining a plurality of said drying hole means therewithin, said second hanging member positioned in telescoping engagement with respect to said first hanging member and movable in a telescopic manner with respect thereto to vary the overall dimensions of said hanging conduit section of said drying fixture means for facilitating usage thereof with articles of various sizes for drying adjacently positioned thereupon;
(c) a set screw means engageable with respect to said first hanging member and said second hanging member for selectively preventing telescoping movement therebetween when fully engaged while allowing telescoping movement therebetween when disengaged; and F. a deodorizing means attachable with respect to any of said drying fixture means to facilitate deodorizing of articles while drying positioned thereupon.

\* \* \* \* \*